(12) United States Patent
Mattson

(10) Patent No.: US 7,277,523 B2
(45) Date of Patent: Oct. 2, 2007

(54) CONTOUR AND SCOUT SCANNING TECHNIQUE FOR PULSED X-RAY LARGE AREA CT DETECTORS

(75) Inventor: Rodney A. Mattson, Mentor, OH (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 48 days.

(21) Appl. No.: 10/560,671

(22) PCT Filed: May 28, 2004

(86) PCT No.: PCT/IB2004/001968

§ 371 (c)(1),
(2), (4) Date: Dec. 14, 2005

(87) PCT Pub. No.: WO2005/000121

PCT Pub. Date: Jan. 6, 2005

(65) Prior Publication Data

US 2007/0092058 A1    Apr. 26, 2007

Related U.S. Application Data

(60) Provisional application No. 60/483,739, filed on Jun. 30, 2003.

(51) Int. Cl.
*A61B 6/00* (2006.01)
(52) U.S. Cl. .................. 378/15; 378/4; 378/16
(58) Field of Classification Search ............ 378/4–20, 378/62, 98.8, 101, 106, 901
See application file for complete search history.

(56) References Cited

U.S. PATENT DOCUMENTS

| | | | |
|---|---|---|---|
| 5,228,070 A | 7/1993 | Mattson | 378/19 |
| 5,379,333 A | 1/1995 | Toth | 378/16 |
| 5,400,378 A | 3/1995 | Toth | 378/16 |
| 5,412,702 A * | 5/1995 | Sata | 378/4 |
| 5,457,724 A | 10/1995 | Toth | 378/4 |
| 5,493,599 A | 2/1996 | Mattson | 378/147 |
| 5,796,802 A | 8/1998 | Gordon | 378/8 |
| 6,067,341 A | 5/2000 | Horiuchi | 378/8 |
| 6,198,790 B1 | 3/2001 | Pflaum | 378/9 |
| 6,289,075 B1 | 9/2001 | Marume | 378/8 |
| 6,763,082 B2 * | 7/2004 | Ozaki | 378/8 |
| 7,023,952 B2 * | 4/2006 | Brunnett | 378/15 |
| 2003/0016778 A1 | 1/2003 | Tachizaki | 378/4 |

FOREIGN PATENT DOCUMENTS

| | | |
|---|---|---|
| EP | 0 531 993 A1 | 3/1993 |
| WO | WO 2004/028369 A2 | 4/2004 |

* cited by examiner

*Primary Examiner*—Jurie Yun

(57) ABSTRACT

A diagnostic imaging system includes an x-ray source (16), which is rotated around an examination region (20). A subject, disposed on a couch (30), is translated longitudinally through the examination region (20). The x-ray source (16) is pulsed at selected angular location(s), e.g. one or both of 6 and 12 o'clock, to transmit x rays through the subject as it is being translated through the examination region (20). The transmitted radiation is being detected by a radiation detector (22) and is reconstructed by an image processor (52) into a two-dimensional projection pilot scan image. A subject contour is calculated and is used along with the radiation attenuation data by a dose calculator (60) to determine the minimum radiation dose required to produce a constant quality image.

22 Claims, 5 Drawing Sheets

CONTOUR AND SCOUT SCANNING TECHNIQUE FOR PULSED X-RAY LARGE AREA CT DETECTORS

CROSS REFERENCE TO RELATED APPLICATIONS

This application claims the benefit of U.S. provisional application Ser. No. 60/483,739 filed Jun. 30, 2003, which is incorporated herein by reference.

The present invention relates to the diagnostic imaging arts. It finds particular application in computed tomography, particularly with a pulsed x-ray source and will be described with particular reference thereto. However, the invention will also find application in other imaging devices with a pulsable, rotating radiation source.

Computed tomography (CT) imaging typically employs an x-ray source that generates a fan-beam, wedge-beam, or cone-beam of x-rays that traverse an examination region. A subject arranged in the examination region interacts with and absorbs a portion of the traversing x-rays. A one- or two-dimensional radiation detector including an array of detector elements is arranged opposite the x-ray source to detect and measure intensities of the transmitted x-rays.

Typically, the x-ray source and the radiation detector are mounted at opposite sides of a rotating gantry such that the gantry is rotated to obtain an angular range of projection views of the subject. In some configurations, the x-ray source is mounted on the rotating gantry while the radiation detector is mounted on a stationary gantry. In either configuration, the projection views are reconstructed using filtered backprojection or another reconstruction method to produce a three-dimensional image representation of the subject or of a selected portion thereof.

Prior to making a CT scan, a pilot scan is conducted to locate the region of interest, precisely determine scan parameters, and the like. The gantry is fixed against rotation and the patient support is moved axially as the x-ray tube is activated to generate a two dimensional projection or pilot scan. Typically, the x-ray tube is fixed at 12 or 6 o'clock as the subject's couch is driven longitudinally. Other times, the x-ray tube is fixed at 3 or 9 o'clock. Sometimes the x-ray tube operates at reduced energy to reduce radiation dose.

There is a continuing demand for CT scanners to rotate at even higher speeds for faster scans. However, it takes a long time or a great amount of energy for the high speed rotating gantry to accelerate to a set velocity and decelerate to a stopping point, making it undesirable to start and stop for the pilot scans. Larger motors for faster acceleration and braking systems for faster deceleration add cost, complexity and unreliability to the scanner. Moreover, some high speed bearings systems are not conducive to stopping at selected stable positions.

The present invention contemplates a new and improved method and apparatus that overcomes the above-reverenced problem and others.

In accordance with one aspect of the present invention, a diagnostic imaging system is disclosed. A means supports a subject. A means translates the supported subject through an examination region. An x-ray source is rotated around the examination region. A means controls pulsing of the x-ray source at a selected angular location around the subject to transmit radiation through the subject as the subject is translated through the examination region. A means detects transmitted radiation, which has passed through the subject. A means reconstructs a pilot scan of the subject from the radiation detected when the x-ray source was pulsed at the selected angular location as the subject was translated through the examination region.

In accordance with another aspect of the present invention, a method is provided for generating a pilot scan. A supported subject is translated through an examination region while an x-ray source is rotated around it. The x-ray source is controlled to pulse at a selected angular location around the subject to transmit radiation through the subject as the subject is translated through the examination region. The radiation, which passed through the subject, is detected by a radiation detector at the selected angular location, as the subject was translated through the examination region.

One advantage of the present invention resides in improved accuracy of patient attenuation profiles.

Another advantage of the present invention resides in more accurate pre-scan profiles and safer x-ray dose profiles to the patient.

Yet another advantage of the present invention is that it can generate a constant image quality scan that can take into account not only patient absorption, but also that of the couch.

Yet another advantage of the present invention resides in reduced cost.

Still further advantages and benefits of the present invention will become apparent to those of ordinary skill in the art upon reading and understanding the following detailed description of the preferred embodiments.

The invention may take form in various components and arrangements of components, and in various steps and arrangements of steps. The drawings are only for purposes of illustrating the preferred embodiments and are not be construed as limiting the invention.

FIG. 1 shows an exemplary diagnostic imaging apparatus employing.

FIG. 2 schematically shows an x-ray source pulsed at 12 o'clock and 6 o'clock as the x-ray source rotates and a subject is linearly translated through an examination region.

FIG. 3 schematically shows the x-ray source pulsed at several angular locations as the x-ray source rotates and the subject is linearly translated through the examination region.

Figure 1:
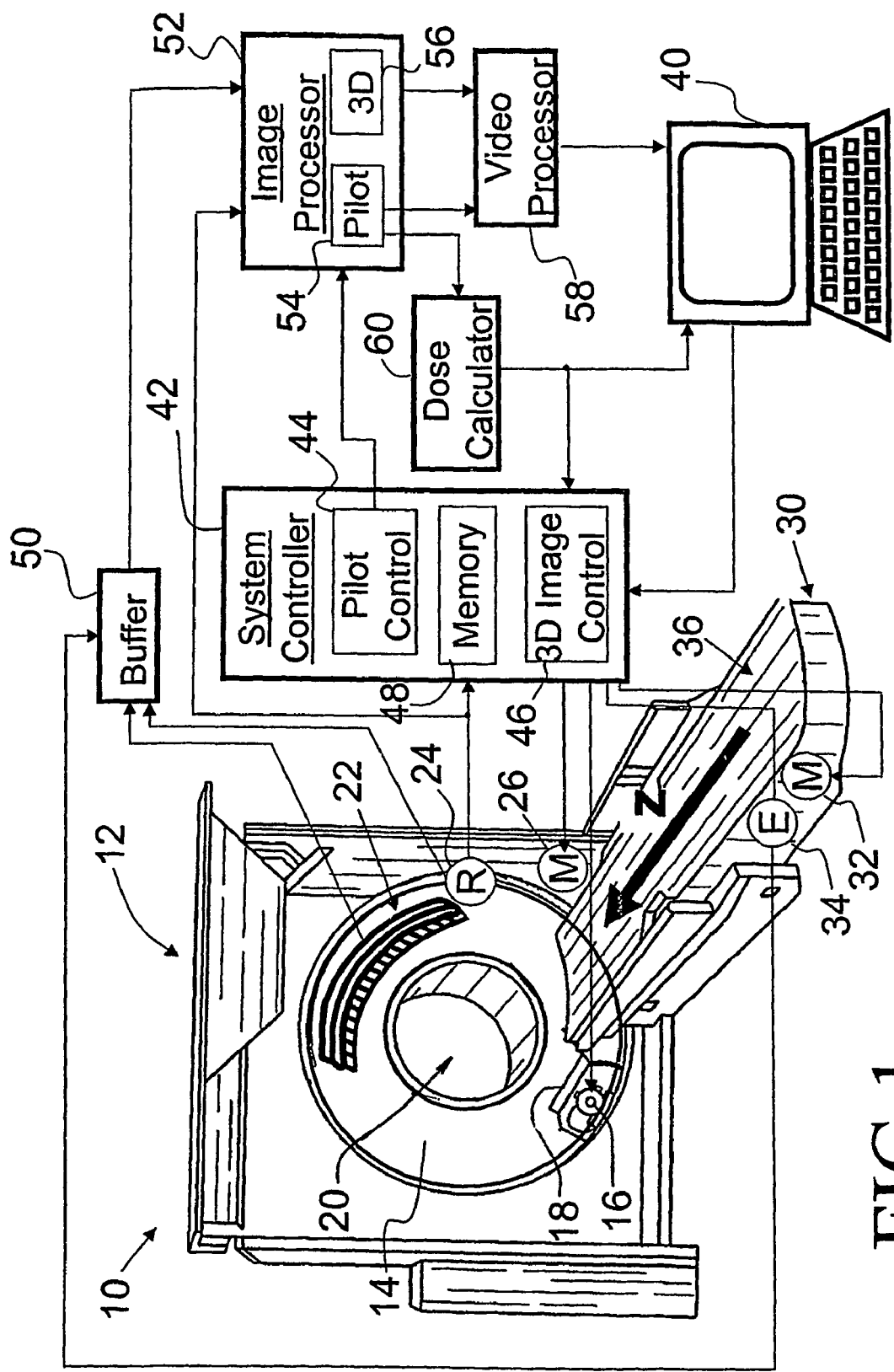

With reference to FIG. 1, a computed tomography (CT) imaging apparatus or scanner 10 includes a stationery gantry 12 that supports a rotating gantry 14. An x-ray source such as x-ray tube 16 and a source collimator 18 cooperate to produce a fan-shaped, cone-shaped, wedge-shaped, or otherwise-shaped x-ray beam directed across an examination region 20 to an array of x-ray detectors 22. Preferably, the x-ray detectors 22 are mounted on the rotating gantry, but may, optionally, be mounted on the stationary gantry surrounding the rotating gantry. A resolver 24 determines an angular orientation of the rotating gantry as it is rotated, preferably at high speed, e.g. 200 rpm, by a motor 26 on high speed mechanical bearings, air bearings, magnetic beatings, or the like.

A subject support or patient couch 30 is driven by a motor 32 to move longitudinally along Z-axis into and through the examination region 20. A encoder 34 monitors movement of a substantially, but not completely, radiotranslucent patent supporting surface 36 of the subject support 30 and provides an electrical output signal indicative of its axial position.

An operator uses a graphical user interface or other user interface means 40 to provide pilot scan parameters, imaging scan parameters, and other parameters to a system controller 42. The system controller controls the motor 26 to control the speed at which the rotating gantry 14 rotates, controls the motor 32 of the patient couch to control advancement and position of the subject. More specifically, the system controller 42 includes a pilot scan controller 44 which controls the gantry and couch motors and the x-ray tube during pilot scans and a 3D image controller 46 which controls these motors and the x-ray tube during volumetric diagnostic imaging scans. Preferably, a scan memory 48 is preloaded with a selection of selectable pilot and imaging scan sequences.

Data from the detector 22 generated during a pilot or volumetric scan is conveyed to a buffer memory 50. The data along with angular gantry position from the resolver 24 and patient couch position from the encoder 34 are supplied to an image processor 52, either directly or through the buffer memory 50. The image processor 52 conveys buffer scan data to a pilot scan processor 54, which generates one or more two-dimensional pilot scan images. During a diagnostic volumetric scan, the image processor 52 conveys the data, angle, and position information to a 3D image processing system 56. Data from the pilot or 3D image processing systems are placed in appropriate form for display by a video processor 58 and conveyed to a display terminal of the user interface 40.

A dose calculation processor 60 analyzes the pilot scan or a region of the pilot scan designated on the user interface to determine recommended scan parameters for the diagnostic imaging scan. The recommended parameters are conveyed to the system controller 42 and are displayed on the user interface 40 so that the operator can review and adjust the recommended scan parameters.

Figure 2:
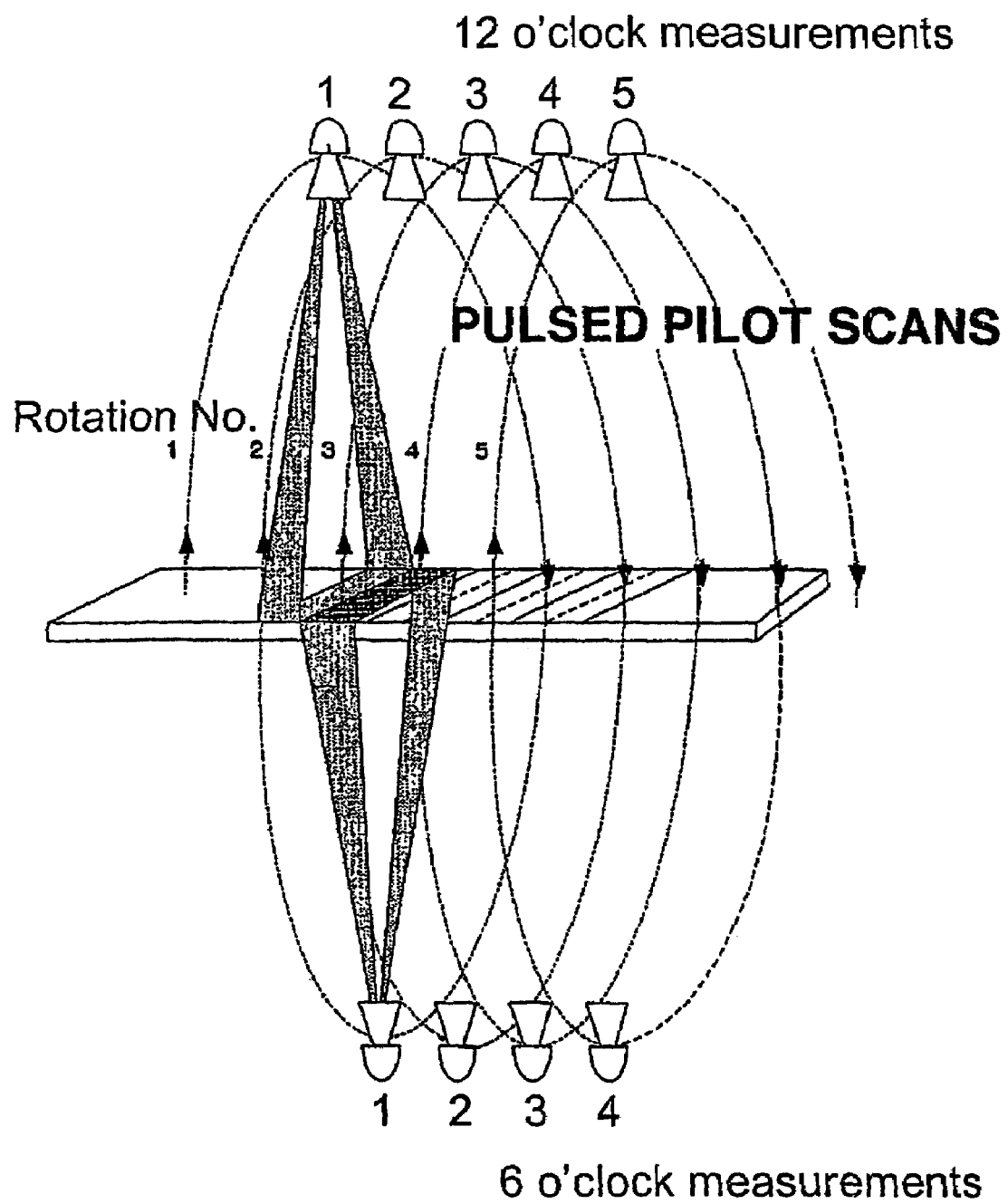

With reference to FIG. 2, in one embodiment, the pilot scan controller pulses the x-ray tube 16 each time the x-ray tube 16 reaches fixed angles, such as 6 o'clock and 12 o'clock. The pilot scan controller further controls the couch motor 32 such that in each half revolution, the couch 30 advances by the irradiated cross-section. Optionally, the 12 o'clock and 6 o'clock scans can overlap, in which case the pilot image processor 54 averages or otherwise blends the overlapping data.

In another embodiment, the x-ray tube 16 is pulsed at only 12 o'clock (or 6 o'clock) and the subject couch 30 is advanced at half the speed.

In another embodiment, the x-ray tube 16 is pulsed at 3 o'clock and 9 o'clock to generate a vertical projection pilot image and a horizontal projection pilot image simultaneously.

Figure 3:
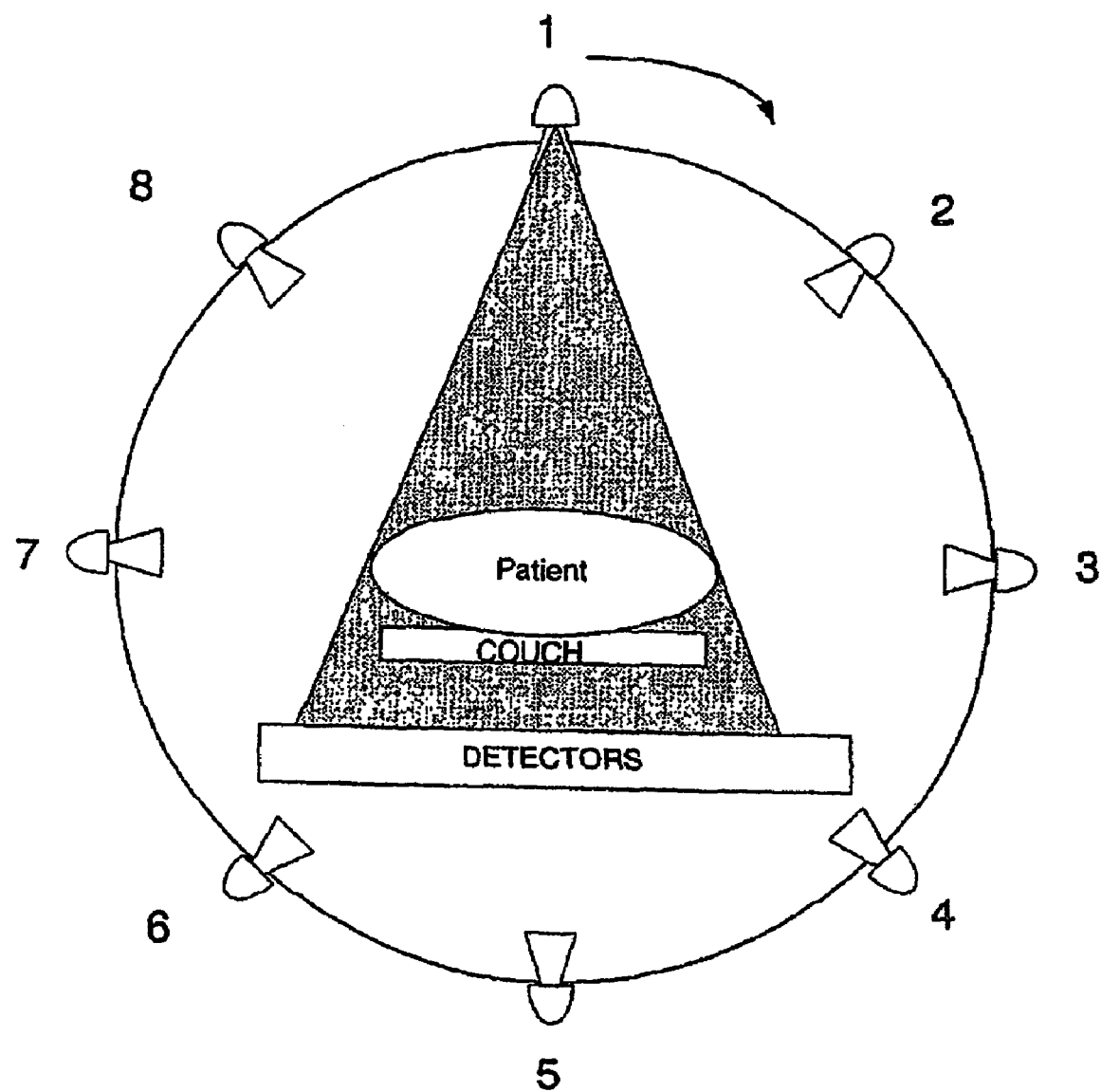

With reference to FIG. 3, in another embodiment, the x-ray tube 16 is pulsed at numerous positions around the patient. Additional pilot images at various angles can be generated. Preferably, the data generated by pulsing the x-ray tube 16 at the additional angles is used to determine the contour of the patient. When the x-ray tube 16 pulsed solely for gaining patient contour information, the x-ray tube 16 can be pulsed at a lower energy to expose the patient to less dosage. When determining the contour, the detected data need only have sufficient gray scale resolution to distinguish between the presence and absence of a subject, and need not discriminate among the various tissues within the patient. The patient contour combined with the projection pilot scans is used by the dose calculation processor 60 to determine patient density as a part of determining the appropriate dose. From the determined dose, a scan parameter calculator 62 determines suggested scan parameters, which are loaded into the scan memory 48 and displayed to the operator on the user interface 40 for review and modification.

Figure 4:
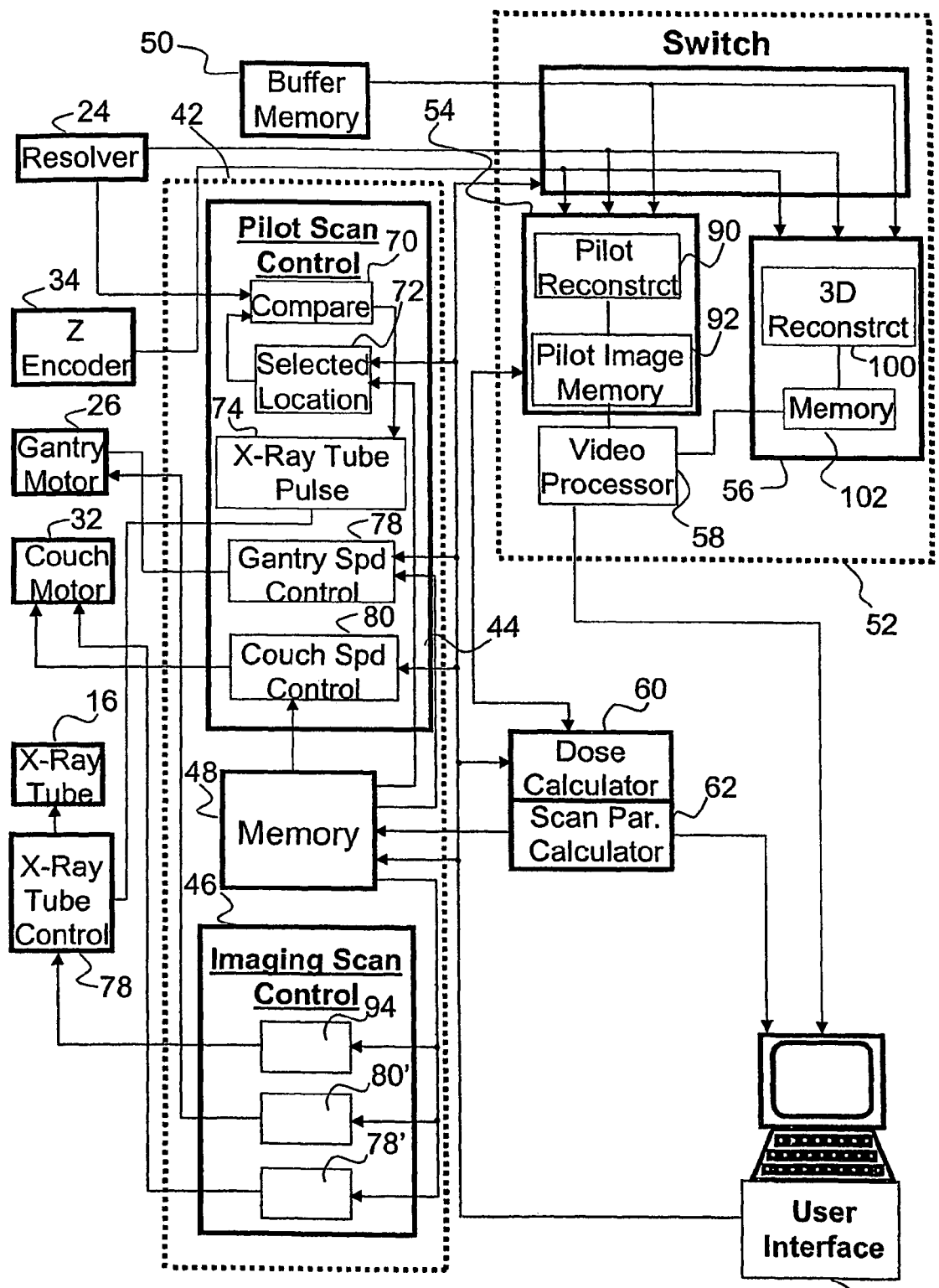
FIG. 4 shows a diagram of the system.

With reference to FIG. 4, an exemplary pilot scan control 44 includes a comparing means 70 for comparing the instantaneous gantry angle with a selected gantry angle from a buffer memory 72, which stores the angles at which the x-ray tube is to be pulsed, as described in conjunction with FIGS. 2 and 3. The buffer memory 72 is loaded either directly from the user interface 40 or from a scan memory 48, which stores a plurality of preselected pilot and imaging scan parameters. Each time the rotating gantry 14 is sensed to reach one of the selected angles, the comparing means 70 causes an x-ray tube pulsing means 74 to cause an x-ray tube control circuit 76 to pulse the x-ray tube 16. A gantry speed control 78 and a couch speed control 80 are controlled either directly from the user interface 40 or with preloaded pilot scan parameters from memory 48 to coordinate the couch advancement with the rotational speeds as discussed above in conjunction with FIG. 2.

A pilot scan reconstruction processor 90 assembles each of the projection pilot scans into a projection image, which is stored in a pilot image memory 92. The video processor 58 selectively withdraws pilot scans from the memory 92 and displays them on the user interface 40. The pilot reconstruction processor 90 also reconstructs the contour of the subject as described above and loads the contour images into the pilot image memory 92. From the contour images and the gray scale, hence density of the projection pilot images, the dose calculation processor 60 calculates recommended imaging scan parameters. These imaging scan parameters are provided to the scan memory 48, which loads the scan parameters into the imaging scan control 46. Preferably, the parameters are also displayed to the operator on the interface 40 to permit the operator to make parameter adjustments, designate a limited region of interest, and the like. An x-ray tube controller 94 causes the x-ray tube control 76 to control the x-ray tube 16 with the selected intensity parameters. A gantry speed controller 78' controls the gantry speed and a couch speed controller 80' controls the couch speed in accordance with the selected imaging scan parameters.

The diagnostic image data from the buffer memory 50 is supplied to the 3D image processor 56. A 3D reconstruction processor 100 reconstructs the diagnostic data into one or more three-dimensional volumetric image representations that are stored in volumetric image memory 102. The video processor 58 withdraws selected portions of the three-dimensional image representations for display on the user interface 40.

Typically, the subject has a non-uniform cross section. Thinner or more penetrable parts of the subject require less radiation for producing the desired image quality. Thicker or less penetrable parts of the subject require more radiation to produce a desired image quality. It is desirable to minimize the radiation dose during CT scan while maintaining a good image quality. In the preferred embodiment, the scan data is collected at a plurality of angular locations. The dose processor 60 determines the optimal radiation dose, based on the pilot scan attenuation data. This will allow planning a low radiation dose, while maintaining a "constant image quality" throughout the scan or series of scans of the subject with the non-uniform cross section.

Figure 5:
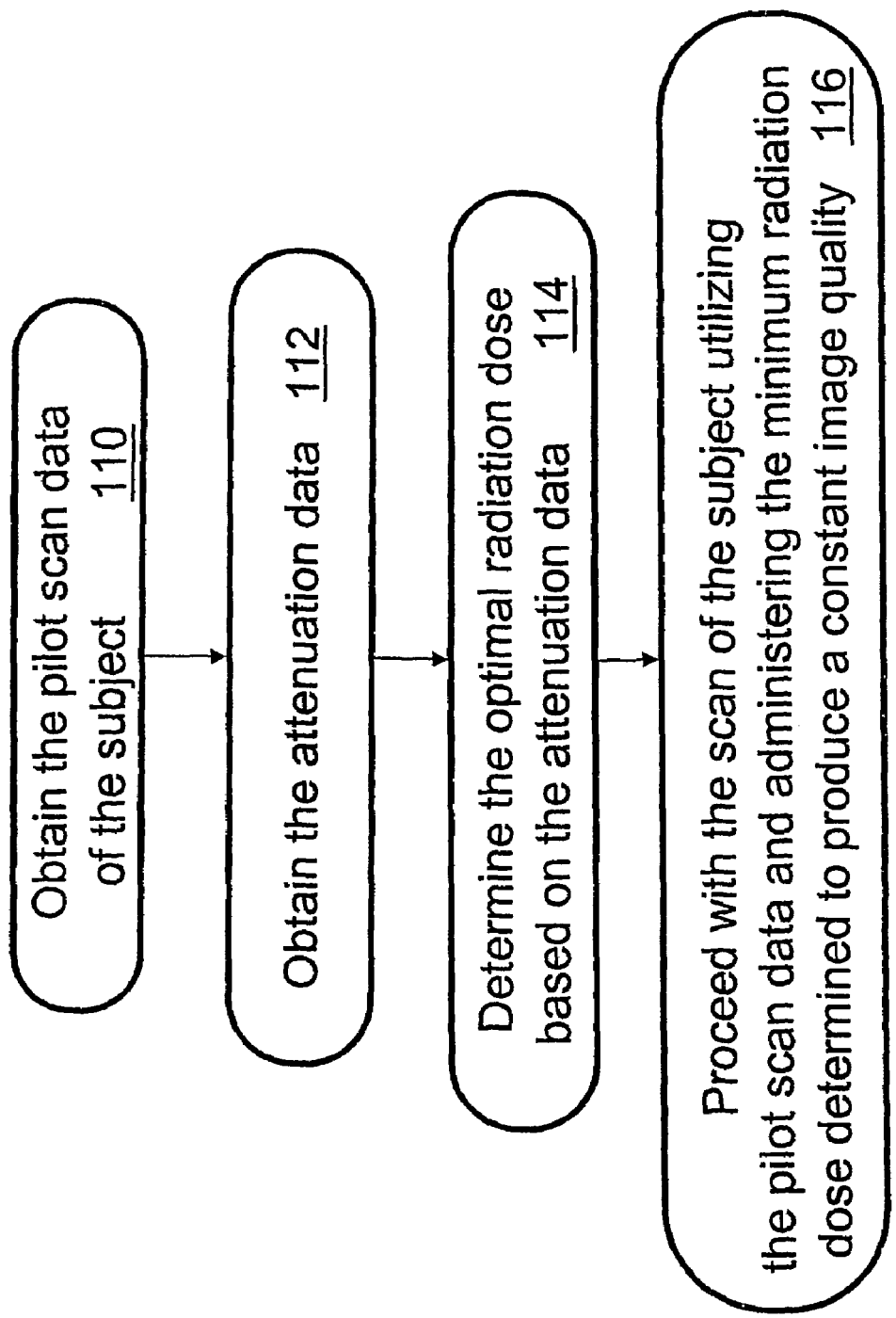
FIG. 5 illustrates a preferred method for generating a pilot scan.

With reference to FIG. 5, after the pilot scan is completed 110, the set of data is obtained that has a relationship between the subject's geometry and the translation of the subject support 30. The attenuation data, indicative of the radiation absorption characteristics of the subject, is obtained 112 and analyzed to produce the optimal radiation dose 114. The operator selects a scan mode of operation and sets the parameters for the scan. The scan is conducted utilizing the pilot scan data and administering the minimum radiation dose determined to produce a constant image quality 116.

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A diagnostic imaging system comprising:
   a means for supporting a subject;
   a means for translating the supporting means through an examination region;
   an x-ray source;
   a means for rotating the x-ray source around the examination region;
   a means for controlling the x-ray source to pulse the x-ray source at a selected angular location around the subject to transmit radiation through the subject as the subject is translated through the examination region;
   a means for detecting transmitted radiation, which has passed through the subject;
   a means for reconstructing a pilot scan of the subject from the radiation detected when the x-ray source was pulsed at the selected angular location as the subject was translated through the examination region; and
   a means for controlling the x-ray source to emit radiation for a computed tomographic scan, wherein the computed tomographic scan is based on the pilot scan and the radiation is detected by the means for detection transmitted radiation; and
   a means for reconstructing volumetric image data based on the radiation detected during the computed tomographic scan.

2. The diagnostic imaging system as set forth in claim 1, wherein the means for controlling the x-ray source to pulse includes an x-ray source controller.

3. The diagnostic imaging system as set forth in claim 1 further including:
   a couch motor control in an operative connection with the translating means to operate the subject supporting means at a selected speed.

4. The diagnostic imaging system as set forth in claim 3, further including:
   a system controller which controls:
      an x-ray source controller to pulse the radiation by the x-ray source at the selected angular orientation, and
      the couch motor control to translate the subject through the examination region in coordination with pulsing of the x-ray tube.

5. The diagnostic imaging system as set forth in claim 4, wherein the system controller and the x-ray source controller cause the x-ray source to pulse at least one of 6 and 12 o'clock in each revolution.

6. The diagnostic imaging system as set forth in claim 5, wherein the radiation is pulsed at both 6 and 12 o'clock.

7. The diagnostic imaging system as set forth in claim 4, wherein the x-ray radiation source controller pulses the radiation source at a plurality of the selected angular locations in each revolution.

8. The diagnostic imaging system as set forth in claim 7, wherein the angular locations are fixed every 9 degrees of rotation.

9. The diagnostic imaging system as set forth in claim 7 further including:
   a means for calculating subject contour.

10. The diagnostic imaging system as set forth in claim 9, wherein the transmitted radiation received by the detection means is indicative of an attenuation of the radiation and further including:
    a means for determining a radiation dose, the radiation dose being determined based on an attenuation data and subject contour.

11. The diagnostic imaging system as set forth in claim 10, further including:
    a means for converting the dose calculations into parameters for the computed tomographic scan.

12. The diagnostic imaging system as set forth in claim 1, further including:
    a stationary gantry defining the subject receiving examination region;
    a rotating gantry which rotates about the examination region; and
    a magnetic bearing for supporting the rotating gantry in the stationary gantry.

13. The diagnostic imaging system of claim 1, wherein the pilot scan is a pre-scan performed prior to performing the computed tomographic procedure, and the scan parameters for the computed tomographic procedure are determined based in part on an image generated from the pilot scan.

14. A method for using a pilot scan to plan a computed tomographic scan, the method comprising:
    supporting and translating a subject support through an examination region;
    rotating a source of an x-ray radiation around the examination region;
    controlling the x-ray source to pulse the x-ray source at a selected angular location around the subject support to transmit radiation through the subject as the subject is translated through the examination region;
    detecting transmitted radiation, which has passed through the subject;
    reconstructing a pilot scan of the subject from the radiation detected when the x-ray source was pulsed at the selected angular location as the subject was translated through the examination region to generate an image; and
    determining scan parameters for a computed tomographic scan based on the image.

15. The method as set forth in claim 14, further including:
    controlling a position and movement of the subject support to operate the subject support at a selected speed and orientation.

16. The method as set forth in claim 14, further including:
    rotating the x-ray source at a selected speed;
    pulsing the x-ray to pass on the radiation through the examination region as the x-ray source rotates through the selected angular location; and,
    moving the subject support in coordinating with the rotating and pulsing of the x-ray source.

17. The method as set forth in claim 16, further including:
    pulsing the x-ray source at least at one of 6 and 12 o'clock in each revolution.

18. The method as set forth in claim 16, further including:
    pulsing the x-ray source at each of 6 and 12 o'clock in each revolution.

19. The method as set forth in claim 16, further including:
    pulsing the x-ray source at a plurality of the selected angular locations in each revolution.

20. The method as set forth in claim 19, wherein the angular locations are fixed every 9 degrees of rotation.

21. The method as set forth in claim 19, further including: calculating a subject contour.

22. The method as set forth in claim 21, wherein the subject has a non-uniform geometry and further including: collecting an attenuation data to produce a subject absorption contour; and determining an optimal radiation dose based on the attenuation data and subject contour to obtain a constant quality image.

* * * * *